US00PP12395P2

(12) United States Plant Patent
Drewlow

(10) Patent No.: US PP12,395 P2
(45) Date of Patent: Feb. 5, 2002

(54) KALANCHOE PLANT NAMED 'FOREVER MIDI FROSTY RED'

(75) Inventor: Lyndon W. Drewlow, Santa Barbara County, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 09/568,415

(22) Filed: May 10, 2000

(51) Int. Cl.[7] ..... A01H 5/00

(52) U.S. Cl. ..... Plt./341

(58) Field of Search ..... Plt./341, 340

*Primary Examiner*—Bruce R. Campell
*Assistant Examiner*—Michelle Kizilkaya
(74) *Attorney, Agent, or Firm*—Webb Ziesenheim Logsdon Orkin & Hanson, P.C.

(57) ABSTRACT

A new Kalanchoe cultivar named 'Forever Midi Frosty Red' characterized by the combined features of red colored flowers and silver-green colored foliage with cream variegation and excellent basal branching.

1 Drawing Sheet

The present invention relates to a new and distinct cultivar of Kalanchoe plant, botanically known as *Kalanchoe blossfeldiana*, and known by the cultivar name 'Forever Midi Frosty Red'. 'Forever Midi Frosty Red' was discovered as a mutation of Keepsake U.S. Plant Pat. No. 7,798) in 1995 in Ashtabula, Ohio. The plant is perennial but typically used as an annual in the floriculture industry.

Asexual reproduction by stem cuttings taken by the inventor in Lompoc, Calif. has shown that the unique features of this new Kalanchoe are stabilized and are reproduced true to type in successive propagations.

The following characteristics distinguish the new Kalanchoe from other cultivated Kalanchoes of this type known to the inventor.

1. 'Forever Midi Frosty Red' has flowers colored Red Group 44A while 'Keepsake' has flowers colored Red Group 45B.

2. 'Forever Midi Frosty Red' has silver-green leaves of Greyed-Green Group 189A with cream variegation at edge of leaf while 'Keepsake' has a solid green leaf of Yellow-Green Group 147A.

3. 'Forever Midi Frosty Red' has a smaller leaf (6 to 7 cm long) than 'Keepsake' (8 to 9 cm long).

4. 'Forever Midi Frosty Red' has an undulate leaf margin while 'Keepsake' has a crenate leaf margin with moderate lobing.

5. 'Forever Midi Frosty Red' has fewer flowers in the flower cluster than 'Keepsake' and is more open.

6. 'Keepsake' is totally male fertile while 'Forever Midi Frosty Red' is mostly male sterile.

The accompanying colored photograph illustrates the overall appearance of this cultivar, as described in detail below, taken as a face view of the plant and showing the colors as true as it is reasonably possible to obtain in a colored reproduction of this type.

The following is a detailed description of the new cultivar, based on plants produced in greenhouses in Lompoc, Calif. during the Winter season of the year. Plants were grown in 10 cm pots and measurements were taken 13 weeks after rooted cuttings were planted. Height measurements were taken from the soil line of the container. The plants were grown at 16° C. night temperatures, 3000–4000 foot candles of light, and 200 ppm nitrogen, 75 ppm potassium, and 200 ppm phosphorous nutritional levels, with trace elements added. Habit of growth, foliage coloration, size of leaves, and peduncle length will be greatly influenced by nutritional and environmental conditions.

Color references are made to The Royal Horticultural Society Colour Chart except where general terms of ordinary dictionary significance are used.

Parentage: Spontaneous mutation of Kalanchoe cultivar Keepsake (U.S. Plant Pat. No. 7,798).

Propagation:

(*A*) *Type cutting.*—Stem tip cuttings up to 3 cm long.

(*B*) *Time to root.*—10 days at 21° C. summer; 12 days at 21° C. winter.

(*C*) *Rooting habit.*—Fine, fibrous, abundant.

Plant description:

*Habit and form of growth.*—Compact, self-branched, excellent basal branching; flower clusters bloom above foliage. Environment and use of growth regulators will play a role in final height. Average height is 15 cm and average width is 20 cm. Internode length is typically 10 mm. Main stem diameter is 10 mm, stem texture is smooth, glabrous, and stem color is Greyed-Green Group 189A.

*Foliage description.*—Leaves simple and opposite with silver-gray cast and cream variegation at edge of leaf. Leaves are petiolate and petioles are Yellow-Green Group 147A having a length of 14 mm and width of 5 mm. Size: Average, full grown leaves on a plant when grown in a 10 cm pot are 6.0 to 7.0 cm long and 4 to 4.5 cm wide. Shape: Ovate with obtuse apex and acute base. Texture: Glabrous; coriaceous and succulent. Margin: Undulate to crenate; shallow lobed. Color: Young foliage top side is Green Group 137B, underside is Greyed-Green Group 191A; mature foliage top side is Greyed-Green Group 189A, underside is between Greyed-Green Groups 191A and 189A and has Yellow-White Group 158B variegation at edge of leaf.

*Branching.*—Average number of lateral branches is 8. The average lateral branch length is 10 cm and average lateral branch diameter is 5 mm. The branch texture is smooth, glabrous, and color is Greyed-Green Group 189A.

Flowering description:

*Flowering habits.*—Inflorescence is a compound dichasial cyme. Terminal flower on main axis opens first followed by the terminal flowers of the side branches, continuing with the subsequent development of branches in the inflorescence. Inflorescence is made up of the main stem and up to 8 or more lateral branches depending on growing schedule followed.

*Natural flowering season.*—Early January. Flowering time under controlled daylength (10 hours daylight, 14 hours darkness) at 20° C. in summer is 8.5 to 9 weeks; in winter is 10 to 10.5 weeks. Flowering time depends on temperature, light intensity and other growing conditions.

*Flower buds.*—Oblong, up to 10 mm long before showing color, developing to tubular as flower petals mature; sheathed in four (4) sepals colored yellow-green. Sepals are individual with a lanceolate shape. Sepals are 8 mm long and 2 mm wide.

*Flowers borne.*—Compound dichasial cyme with primary peduncle being 3 mm in diameter just below the first branch of the inflorescence; length of peduncle will vary depending on growing conditions. The average number of peduncles is 10 with an average length of 8 cm, average diameter of 4 mm, smooth, glabrous texture, and Yellow-Green Group 147A color. The average number of pedicels is 200 with an average length of 3 mm, average diameter of 1 mm, smooth glabrous texture, and Yellow-Green Group 147A. Pedicels vary in length depending on where they are in the inflorescence.

*Quantity of flowers.*—Numerous flowers on the main stem plus the 8 or more lateral branches will have 25 or more flowers each. Approximate time period for bloom lastingness is 4 to 6 weeks. The florets are flat in shape.

*Petals.*—Shape: Semi-rounded, top cuspidate. Color: Top side when opening is Red Group 45B, deepening to Red Group 44A. Underside is Red Group 36B. Number of petals: 4.

*Reproductive organs.*—Stamens: 8 in number, with an average size of 3 mm not fused to the petal. Anthers. Flat, elliptical in shape, yellow-green in color. Filament color: Yellow-green. Pollen: Scarce, yellow in color; most anthers are sterile. Pistils: Average of 4 per flower with an average size of 12 mm. Stigma: Flat in shape, mature color is white with red-purple tint. Style color: Light green. Ovaries: 4 in number, size 5 mm, green color.

*Fertility.*—The plants are fertile, but do not normally set seed under greenhouse or garden conditions, unless in a controlled crossing program.

Disease resistance: 'Forever Midi Frosty Red' has shown resistance to powdery mildew. No disease problems have been observed to date.

OTHER IMPORTANT CHARACTERISTICS

1. 'Forever Midi Frosty Red' is a unique Kalanchoe cultivar having silver-green foliage with cream variegation at edge of leaves.

2. Due to highly branched, compact growth habit can be finished in a 10 cm pot without use of growth regulators.

3. Pinching is not required or recommended.

I claim:

1. A new and distinct cultivar of Kalanchoe plant named 'Forever Midi Frosty Red', as illustrated and described.

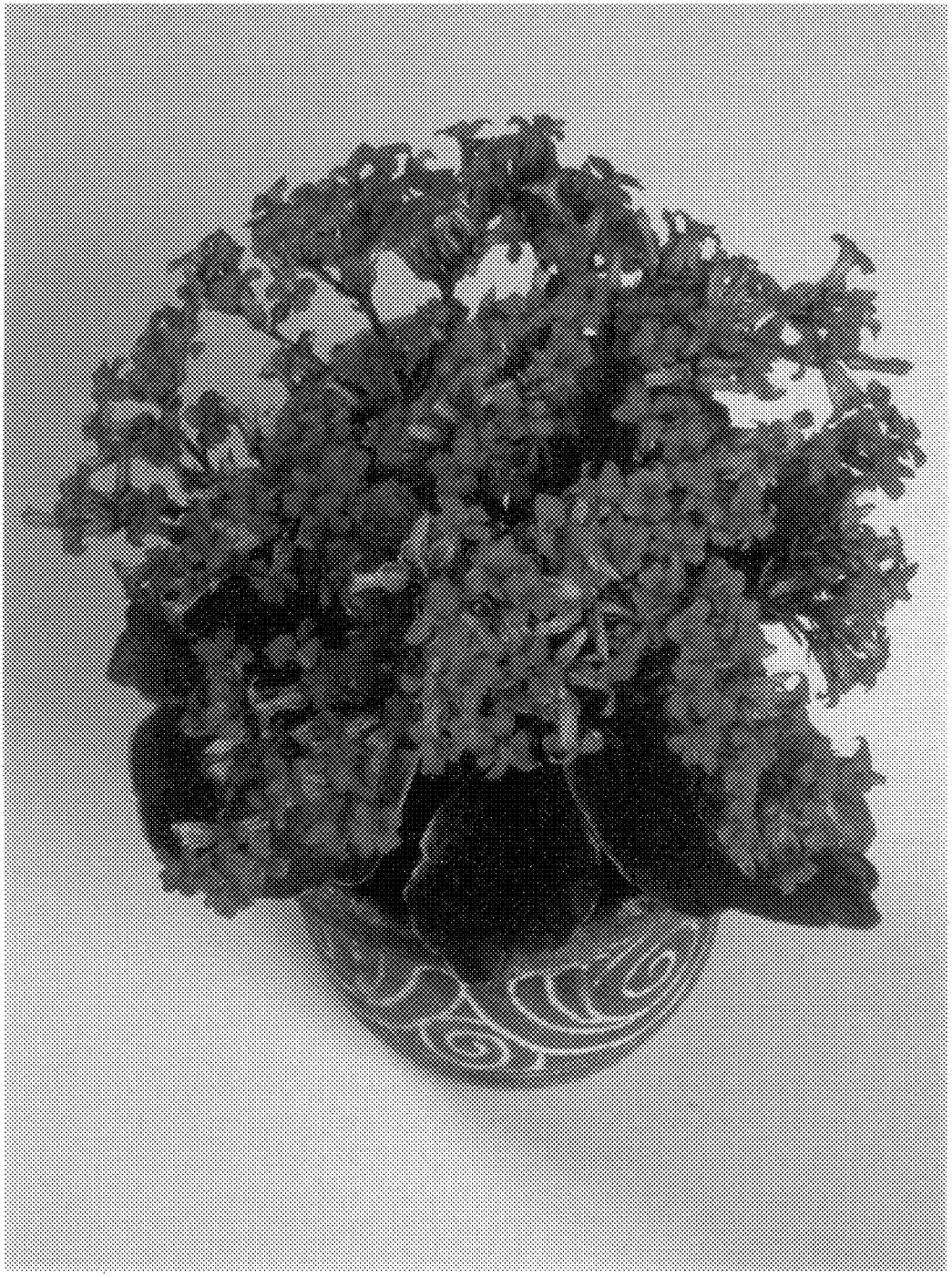

* * * * *